(12) United States Patent
Su et al.

(10) Patent No.: US 10,654,965 B2
(45) Date of Patent: May 19, 2020

(54) METHOD OF PRODUCING FIVE-CARBON RING-CONTAINING COMPOUND AND FIVE-CARBON RING DERIVATIVE-CONTAINING POLYURETHANE, AND FIVE-CARBON RING DERIVATIVE-CONTAINING POLYURETHANE

(71) Applicant: NATIONAL CHUNG SHAN INSTITUTE OF SCIENCE AND TECHNOLOGY, Taoyuan (TW)

(72) Inventors: Wen-Chiung Su, Taoyuan (TW); Chien-Hsin Wu, Taipei (TW); Yu-Ru Lin, Taipei (TW); Sheng-Hong Dai, Taipei (TW); Ru-Jong Jeng, Taipei (TW)

(73) Assignee: NATIONAL CHUNG SHAN INSTITUTE OF SCIENCE AND TECHNOLOGY (TW)

( * ) Notice: Subject to any disclaimer, the term of this patent is extended or adjusted under 35 U.S.C. 154(b) by 188 days.

(21) Appl. No.: 15/828,457

(22) Filed: Dec. 1, 2017

(65) Prior Publication Data
US 2019/0048123 A1 Feb. 14, 2019

(30) Foreign Application Priority Data
Aug. 10, 2017 (TW) .............................. 106126996 A

(51) Int. Cl.
*C08G 18/32* (2006.01)
*C07C 39/17* (2006.01)
(Continued)

(52) U.S. Cl.
CPC ............ *C08G 18/3215* (2013.01); *C07C 4/22* (2013.01); *C07C 13/61* (2013.01); *C07C 37/14* (2013.01); *C07C 39/17* (2013.01); *C07C 41/16* (2013.01); *C08G 18/3212* (2013.01); *C08G 18/4269* (2013.01); *C08G 18/4283* (2013.01); *C08G 18/73* (2013.01); *C08G 18/755* (2013.01); *C08G 18/758* (2013.01); *C08G 18/7671* (2013.01);
(Continued)

(58) Field of Classification Search
CPC ............ C08G 18/3212; C08G 18/3215; C08G 18/7657
See application file for complete search history.

(56) References Cited

U.S. PATENT DOCUMENTS

| 4,246,367 A | 1/1981 | Curtis, Jr. |
| 4,301,306 A | 11/1981 | Layer |

(Continued)

OTHER PUBLICATIONS

"Synthesis of Diols Containing Cyclopentane Card-Type Groups and Polyurethanes on Their Basis" to Papava et al. Proceedings of the Georgian Academy of Sciences, vol. 32, Issue 1-2, pp. 98-103, 2006.*

*Primary Examiner* — Michael L Leonard
(74) *Attorney, Agent, or Firm* — Schmeiser, Olsen & Watts, LLP

(57) ABSTRACT

A method of producing a five-carbon ring derivative-containing polyurethane involves introducing a DCPD-derived 5-carbon cyclic compound into a polyurethane material and effectuating polymerization in the presence of a solvent of a low boiling point and low toxicity to produce a five-carbon ring derivative-containing polyurethane of a high molecular weight.

7 Claims, 9 Drawing Sheets

(51) Int. Cl.
*C07C 13/61* (2006.01)
*C08G 18/42* (2006.01)
*C07C 41/16* (2006.01)
*C08G 18/75* (2006.01)
*C08G 18/73* (2006.01)
*C08G 18/76* (2006.01)
*C07C 37/14* (2006.01)
*C07C 4/22* (2006.01)

(52) U.S. Cl.
CPC ...... *C07C 2601/10* (2017.05); *C08G 18/7657* (2013.01)

(56) References Cited

U.S. PATENT DOCUMENTS

| | | | |
|---|---|---|---|
| 4,447,591 A * | 5/1984 | Watanabe | C08G 63/08 528/354 |
| 4,764,571 A | 8/1988 | Namba et al. | |
| 6,180,696 B1 | 1/2001 | Wong et al. | |
| 2018/0010024 A1* | 1/2018 | Lu | C08G 18/6625 |

* cited by examiner

A method of producing a five-carbon ring-containing compound

A method of producing a five-carbon ring derivative-containing polyurethane

METHOD OF PRODUCING FIVE-CARBON RING-CONTAINING COMPOUND AND FIVE-CARBON RING DERIVATIVE-CONTAINING POLYURETHANE, AND FIVE-CARBON RING DERIVATIVE-CONTAINING POLYURETHANE

CROSS-REFERENCE TO RELATED APPLICATION

This non-provisional application claims priority under 35 U.S.C. § 119(a) on Patent Application No(s). 106126996 filed in Taiwan, R.O.C. on Aug. 10, 2017, the entire contents of which are hereby incorporated by reference.

FIELD OF THE INVENTION

The present invention relates to methods of producing a polyurethane and, more particularly, to a 5-carbon cyclic compound, five-carbon ring derivative-containing polyurethane, and a method of producing the same.

BACKGROUND OF THE INVENTION

Five-carbon alkene is a by-product of a process of degrading fossil hydrocarbons to ethylene at high temperature, and its content makes up 12%~20% of the ethylene produced; hence, it is worth being processed. At normal temperature, five-carbon alkene exists in the form of dicyclopentadiene (DCPD). A raw material and five-carbon alkene undergo polymerization in the presence of a catalyst to produce a thermosetting polymer which hardly deforms but is wholly aliphatic. Thanks to two double bonds of DCPD, it is feasible to produce a 5-carbon cyclic functional reaction intermediate for undergoing polymerization and thereby producing various polymers. U.S. Pat. No. 4,301,306 A discloses using phenol derivative to react with DCPD and produce a series of resin materials for norbornene phenol. U.S. Pat. No. 4,246,367A discloses producing highly reactive polyester from DCPD. Both U.S. Pat. Nos. 4,764,571 A and 6,180,696 B1 disclose producing monomers of anhydrides and epoxy resins from DCPD to undergo polymerization and thus produce functional polymer materials.

SUMMARY OF THE INVENTION

As indicated by the aforesaid citation documents, DCPD is convenient to process and thus is a promising green material. However, the industrial sector has not hitherto undertaken any research in which a DCPD-derived 5-carbon cyclic compound is used as a chain extender to produce five-carbon ring derivative-containing polyurethane.

In view of the aforesaid drawbacks of the prior art, it is an objective of the present invention to provide a 5-carbon cyclic compound and a method of producing the same, as well as a five-carbon ring derivative-containing polyurethane and a method of producing the same. The method involves degrading dicyclopentadiene (DCPD) to a diene precursor of 5-carbon cyclic compound-containing cyclopentadiene (CPD) and then allowing CPD to undergo a series of reactions, including translocation, alkylation and addition, and thereby produce five-carbon ring-containing glycol monomers, and treating the monomers as a polyurethane chain extender, thereby producing five-carbon ring derivative-containing polyurethane material.

In order to achieve the above and other objectives, the present invention provides a method of producing a five-carbon ring-containing compound expressed by formula (I), the method comprising the steps of: (1) degrading dicyclopentadiene to cyclopentadiene, followed by allowing cyclopentadiene to react with phenol by acid catalysis to produce 4-(cyclopent-2-enyl)phenol; (2) allowing 4-(cyclopent-2-enyl)phenol to react in presence of a phosphoric acid catalyst to produce 4-cyclopentenylphenol; and (3) allowing 4-cyclopentenylphenol to react with phenol by acid catalysis to produce a compound expressed by formula (I) below,

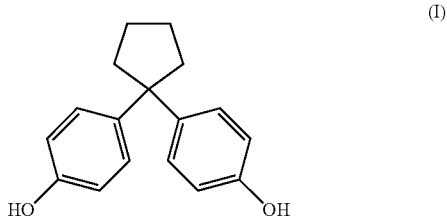 [SMILES: Oc1ccc(C2(c3ccc(O)cc3)CCCC2)cc1]

(I)

In an embodiment of the present invention, a solvent in step (1) or step (2) is toluene.

In an embodiment of the present invention, the catalyst in step (2) is PdCl2(PhCN)2, and the reaction temperature is 130-150° C.

In an embodiment of the present invention, the reaction temperature in step (3) is 70-90° C.

In an embodiment of the present invention, the acid in step (1) or step (3) is phosphoric acid ($H_3PO_4$) or hydrochloric acid (HCl).

In an embodiment of the present invention, the compound expressed by formula (I) reacts with ethylene carbonate, using sodium hydroxide as a catalyst, to produce a compound expressed by formula (II) below.

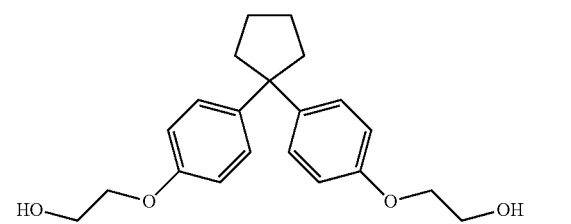

(II)

In an embodiment of the present invention, the compound expressed by formula (I) reacts with propylene carbonate, using sodium hydroxide as a catalyst, to produce a compound expressed by formula (III) below.

(III)

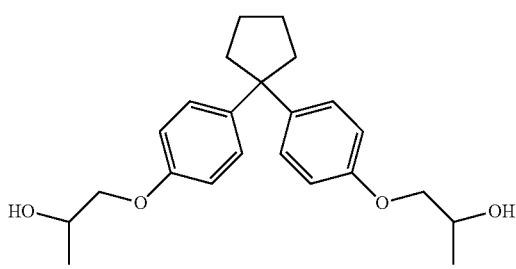

The present invention further provides a method of producing a five-carbon ring derivative-containing polyurethane, the method comprising the steps of: (a) allowing a diisocyanate compound to react with a polyethylene glycol compound in a solvent and thus produce a prepolymer; and (b) allowing the prepolymer to react continuously with a 5-carbon cyclic compound expressed by one of formula (I), formula (II) and formula (III) and thus produce a five-carbon ring derivative-containing polyurethane.

In an embodiment of the present invention, in step (a), the diisocyanate compound is one selected from the group consisting of methylene di-p-phenyl diisocyanate, 1,6-hexamethylene diisocyanate, isophorone diisocyanate, dicyclohexylmethane-4-4'-diisocyanate, and a combination thereof, and the polyethylene glycol compound is one selected from the group consisting of polyester glycol, polyether glycol, and a combination thereof, where the polyester glycol is polycaprolactone (PCL).

In an embodiment of the present invention, in step (b), the reaction duration is 3-6 hours.

In an embodiment of the present invention, in step (a) and step (b), a solvent is acetone or tetrahydrofuran.

In an embodiment of the present invention, the five-carbon ring derivative-containing polyurethane has a molecular weight of 55,000~200,000.

In an embodiment of the present invention, if the diisocyanate compound is methylene di-p-phenyl diisocyanate (MDI), and the polyethylene glycol compound is polycaprolactone (PCL), the five-carbon ring derivative-containing polyurethane is a polymer expressed by formula (IV) below, -continued

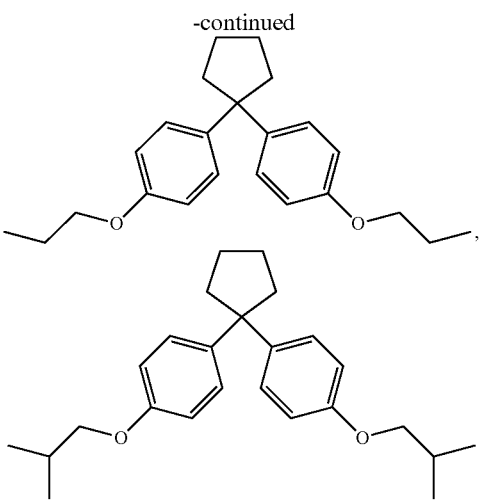

and where y>0.

In an embodiment of the present invention, regarding the five-carbon ring derivative-containing polyurethane, n segment has a molecular weight of 1,000~4,000, and x segment to y segment weight ratio is expressed by y/(x+y)=0.4~0.6.

The present invention not only uses a green environment-friendly material (dicyclopentadiene, DCPD) to produce glycol monomers of a five-carbon ring-containing compound, but also uses the monomers as a chain extender for use in polymerization to form polyurethane and thereby produce a five-carbon ring derivative-containing polyurethane material. Unlike the prior art which uses high-polarity, high-boiling-point dimethylformamide (DMF) or dimethylacetamide (DMAc) as a synthetic solvent for use in polymerization to form polyurethane, the present invention provides a production method which involves carrying out polymerization in a solvent (such as tetrahydrofuran or acetone) with a low boiling point and low toxicity to form polyurethane which has a high molecular weight.

The above summary, the detailed description below, and the accompanying drawings further explain the technical means and measures taken to achieve predetermined objectives of the present invention and the effects thereof. The (IV)

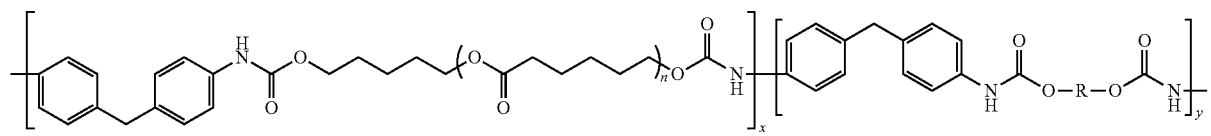

where R is one of the groups below,

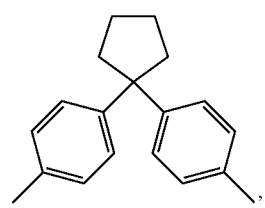

other objectives and advantages of the present invention are explained below and illustrated with the accompanying drawings.

DETAILED DESCRIPTION OF THE PREFERRED EMBODIMENTS

Implementation of the present invention is hereunder illustrated by a specific embodiment. Persons skilled in the art can easily understand other advantages and effects of the present invention by referring to the disclosure contained in the specification.

Figure 1:
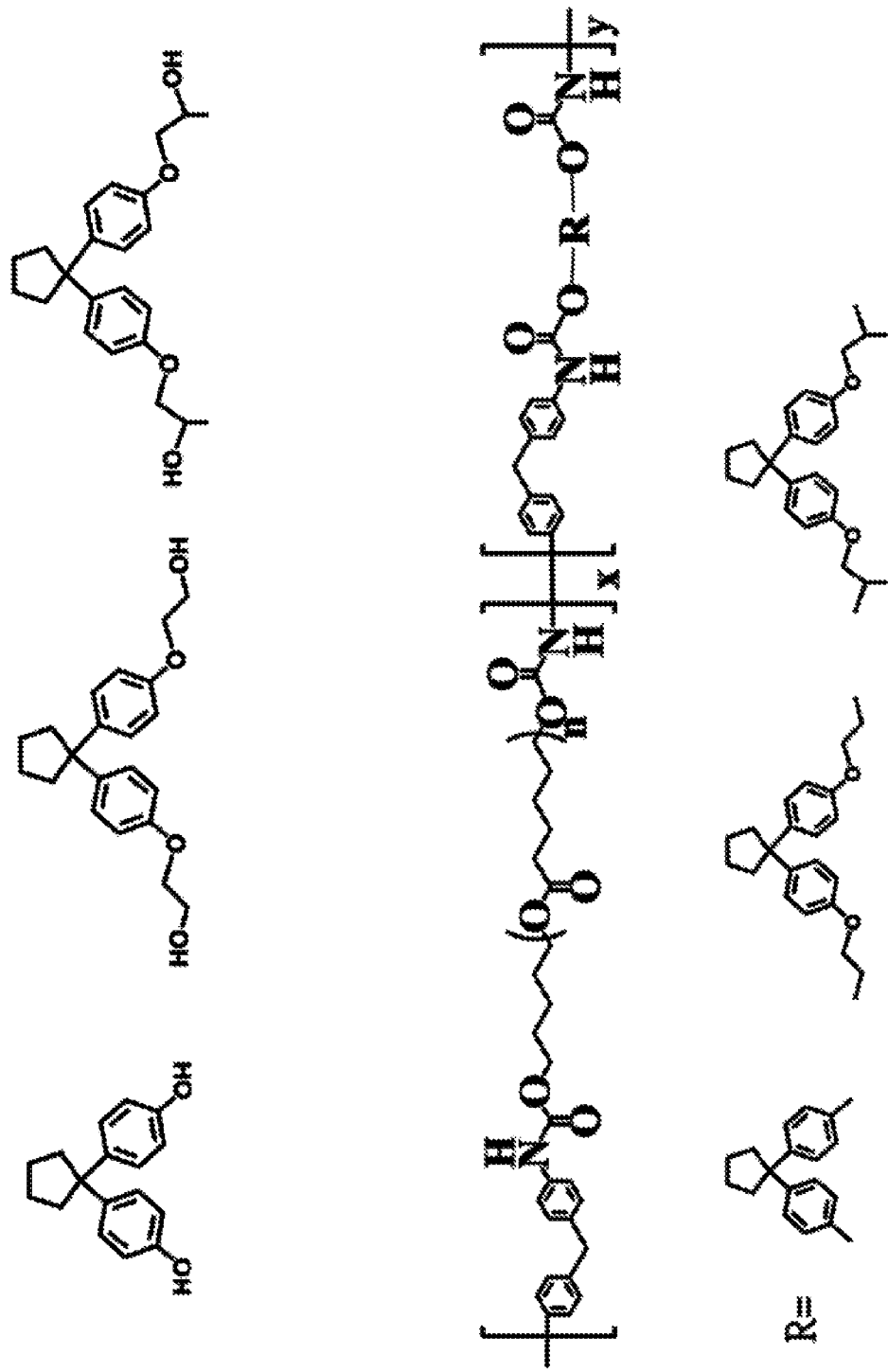
FIG. 1 shows structural formulas of a 5-carbon cyclic compound and five-carbon ring derivative-containing polyurethane of the present invention.
Figure 2:
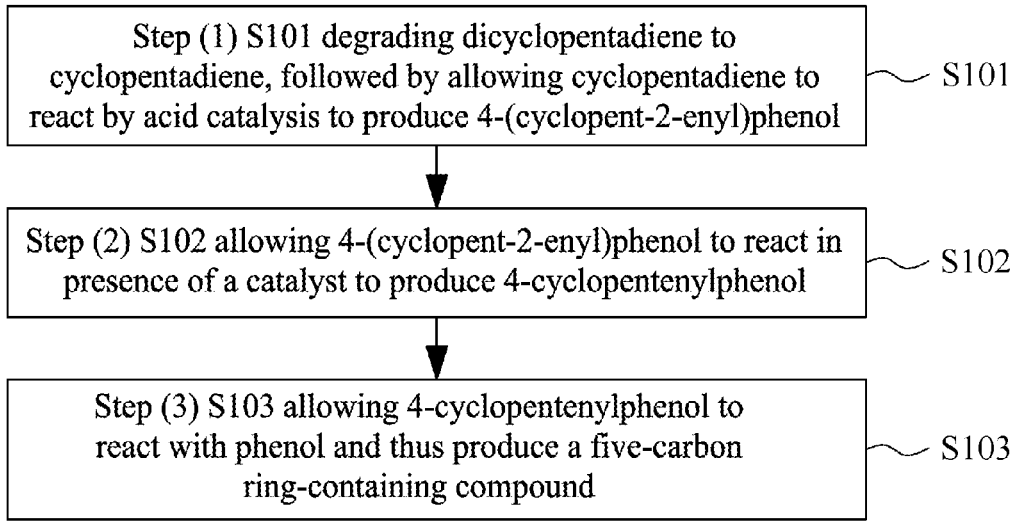
FIG. 2 is a schematic view of the process flow of a method of producing the 5-carbon cyclic compound and five-carbon ring derivative-containing polyurethane according to an embodiment of the present invention.
Figure 2:
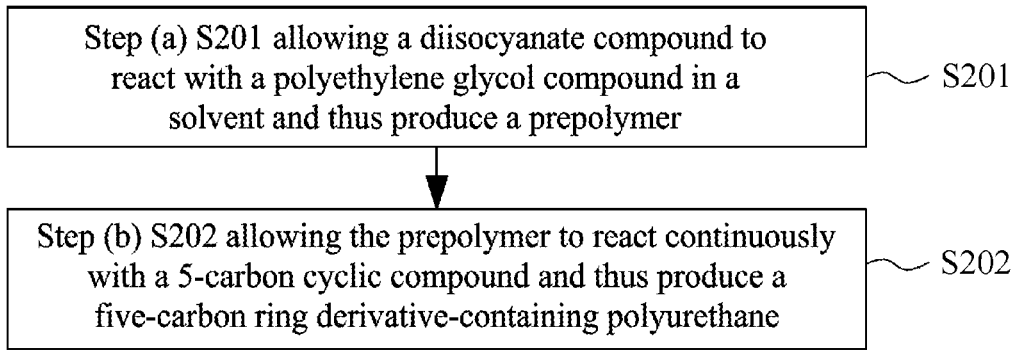

Referring to FIG. 2, there is shown a schematic view of the process flow of a method of producing the 5-carbon cyclic compound and five-carbon ring derivative-containing polyurethane according to an embodiment of the present invention. As shown in the diagram, the method of producing a five-carbon ring-containing compound according to an embodiment of the present invention comprises the steps of: (1) degrading dicyclopentadiene to cyclopentadiene, followed by allowing cyclopentadiene to react with phenol by acid catalysis to produce 4-(cyclopent-2-enyl)phenol; (2) allowing 4-(cyclopent-2-enyl)phenol to react in presence of a catalyst to produce 4-cyclopentenylphenol; and (3) allowing 4-cyclopentenylphenol to react with phenol by acid catalysis to produce a compound expressed by formula (I) below.

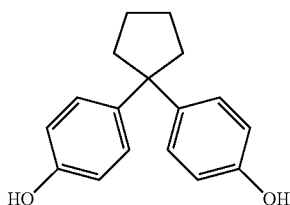

(I)

The method of the present invention further comprises allowing the compound expressed by formula (I) to react with ethylene carbonate, using sodium hydroxide as a catalyst, to produce a compound expressed by formula (II) below.

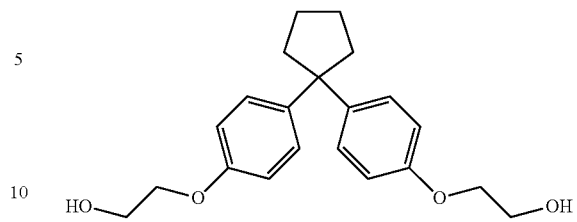

(II)

The method of the present invention further comprises allowing the compound expressed by formula (I) to react with propylene carbonate, using sodium hydroxide as a catalyst, to produce a compound expressed by formula (III) below.

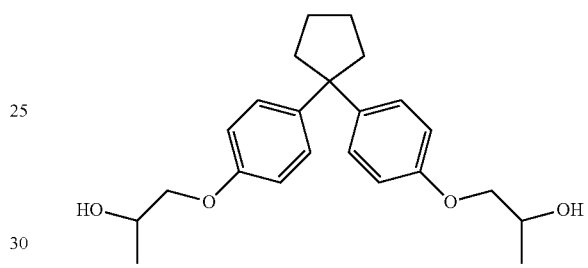

(III)

As shown in FIG. 2, the present invention further provides a method of producing a five-carbon ring derivative-containing polyurethane, the method comprising the steps of: (a) allowing a diisocyanate compound to react with a polyethylene glycol compound in a solvent and thus produce a prepolymer; and (b) allowing the prepolymer to react continuously with a 5-carbon cyclic compound expressed by one of formula (I), formula (II) and formula (III) and thus produce a five-carbon ring derivative-containing polyurethane.

Embodiment

Figure 3:
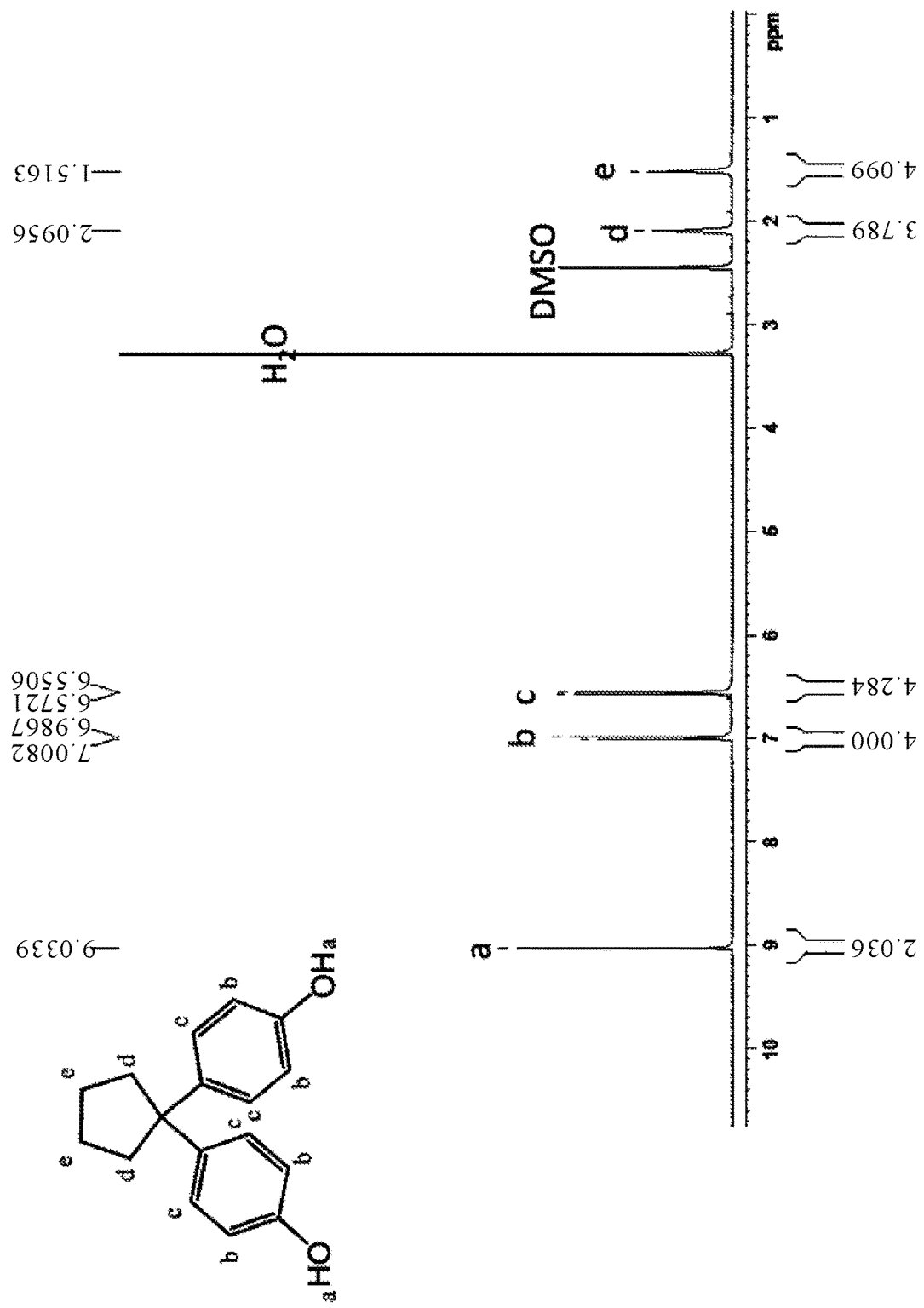
FIG. 3 is a $^1$H-NMR spectrum of the 5-carbon cyclic compound according to embodiment 1 of the present invention.

Embodiment 1: degrade dicyclopentadiene (DCPD) to cyclopentadiene (CPD), dissolve 33 g of CPD in 100 ml of toluene, allow CPD to react with phenol in the presence of phosphoric acid (H$_3$PO$_4$) for 2 hours to obtain a crude product, neutralize the crude product with sodium carbonate, perform filtration and purification on the neutralized crude product to obtain a mixture of ortho- and para-phenol cyclopentenylphenol, which then undergoes separation by distillation to obtain para product 4-(cyclopent-2-enyl)phenol. Afterward, dissolve 3 g of 4-(cyclopent-2-enyl)phenol in 30 ml of toluene, add 0.15 g of catalyst PdCl$_2$(PhCN)$_2$, and allow them to react at 130-150° C. for 2 hours. Subsequent purification and recrystallization yields a product, i.e., 4-cyclopentenylphenol. At last, put 0.5 g of 4-cyclopentenylphenol in a 50 ml two-neck round-bottom flask, and add thereto 2.94 g of phenol as a reactant, allowing them to react in the presence of 1M HCl at 80° C. for 24 hours. Afterward, the crude product is neutralized and then purified to obtain 4,4'-(cyclopentane-1,1-diyl)diphenol(CPDP) presented in the form of dark red powder and expressed by formula (I). Referring to FIG. 3, there is shown a $^1$H-NMR spectrum of the 5-carbon cyclic compound according to embodiment 1 of the present invention. As shown in the diagram, hydrogen signals are absent from 6 ppm of alkene tertiary carbon, indicating thorough reaction and complete purification.

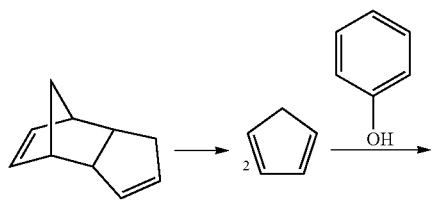

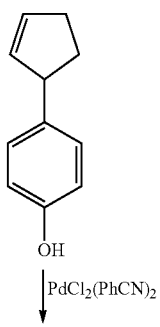

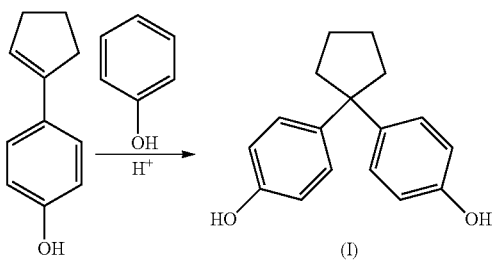

Figure 4:
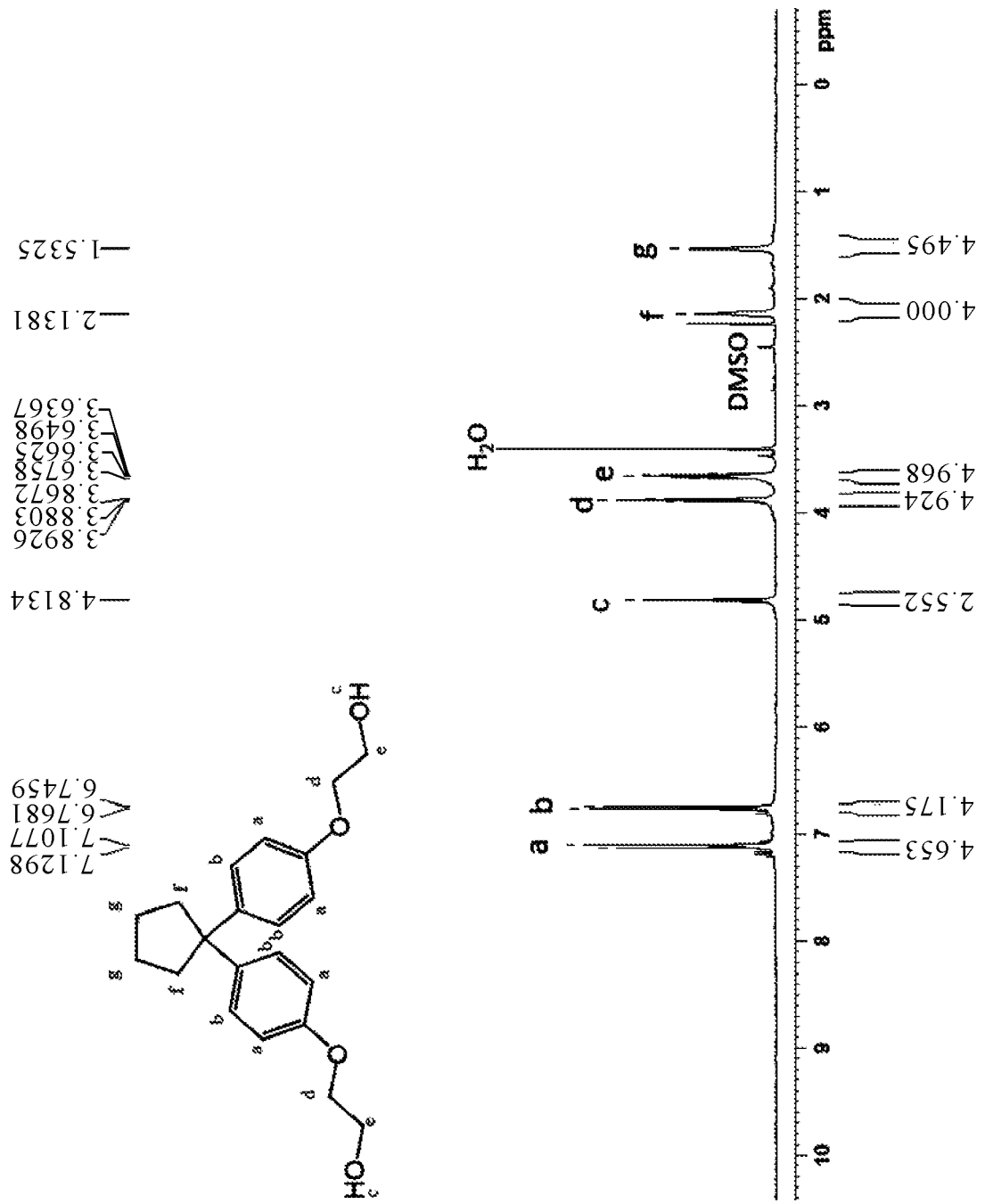
FIG. 4 is a $^1$H-NMR spectrum of the 5-carbon cyclic compound according to embodiment 2 of the present invention.

Embodiment 2: add 0.5 g of CPDP monomers to ethylene carbonate, and allow them to react in a nitrogen atmosphere for 24 hours in the presence of sodium hydroxide as a catalyst. Afterward, the crude product is neutralized and then purified to obtain 2,2'-(4,4'-(cyclopentane-1,1-diyl)bis(4,1-phenylene))bis(oxy)diethanol presented in the form of white powder and expressed by formula (II). Referring to FIG. 4, there is shown a ¹H-NMR spectrum of the 5-carbon cyclic compound according to embodiment 2 of the present invention. As shown in the diagram, hydrogen signals are absent from 6 ppm of alkene tertiary carbon, but 3.5 ppm and 3.9 ppm of primary alcohol extension signals are generated, respectively, indicating thorough reaction and complete purification.

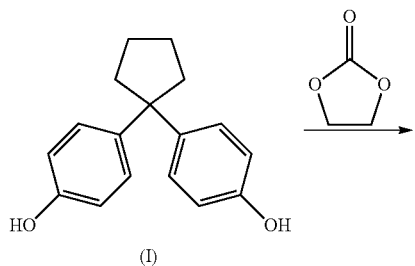

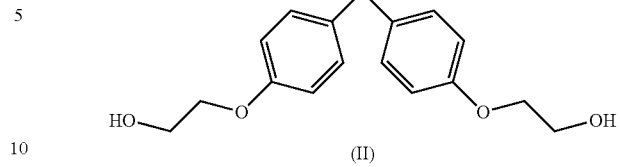

Figure 5:
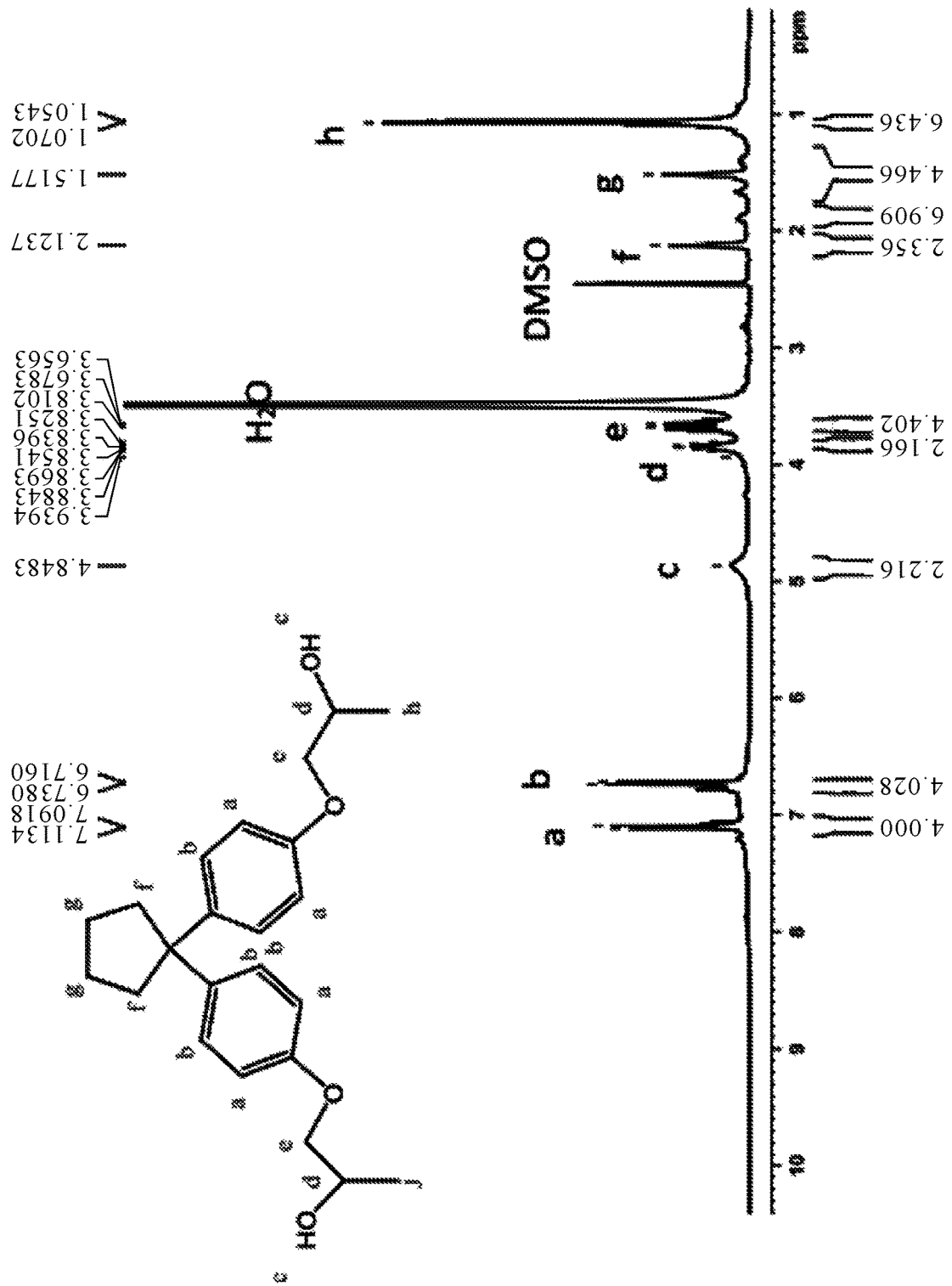
FIG. 5 is a $^1$H-NMR spectrum of the 5-carbon cyclic compound according to embodiment 3 of the present invention.

Embodiment 3: add 0.5 g of CPDP monomers to propylene carbonate, and allow them to react in a nitrogen atmosphere for 24 hours in the presence of sodium carbonate as a catalyst. Afterward, the crude product is baked and dried to obtain 1,1'-(4,4'-(cyclopentane-1,1-diyl)bis(4,1-phenylene))bis(oxy)dipropan-2-ol presented in the form of pale brown powder and expressed by formula (III). Referring to FIG. 5, there is shown a ¹H-NMR spectrum of the 5-carbon cyclic compound according to embodiment 3 of the present invention. As shown in the diagram, hydrogen signals are absent from 6 ppm of alkene tertiary carbon, but 1.1 ppm, 3.7 ppm and 3.9 ppm secondary alcohol extension signals are generated, respectively, indicating thorough reaction and complete purification.

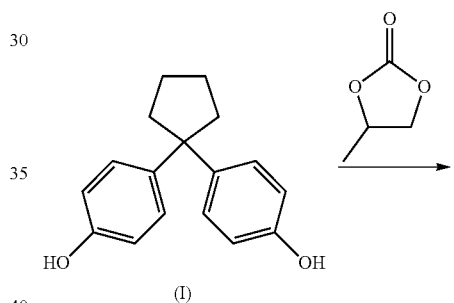

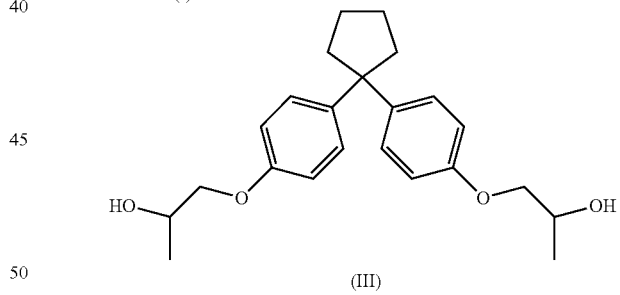

Figure 6:
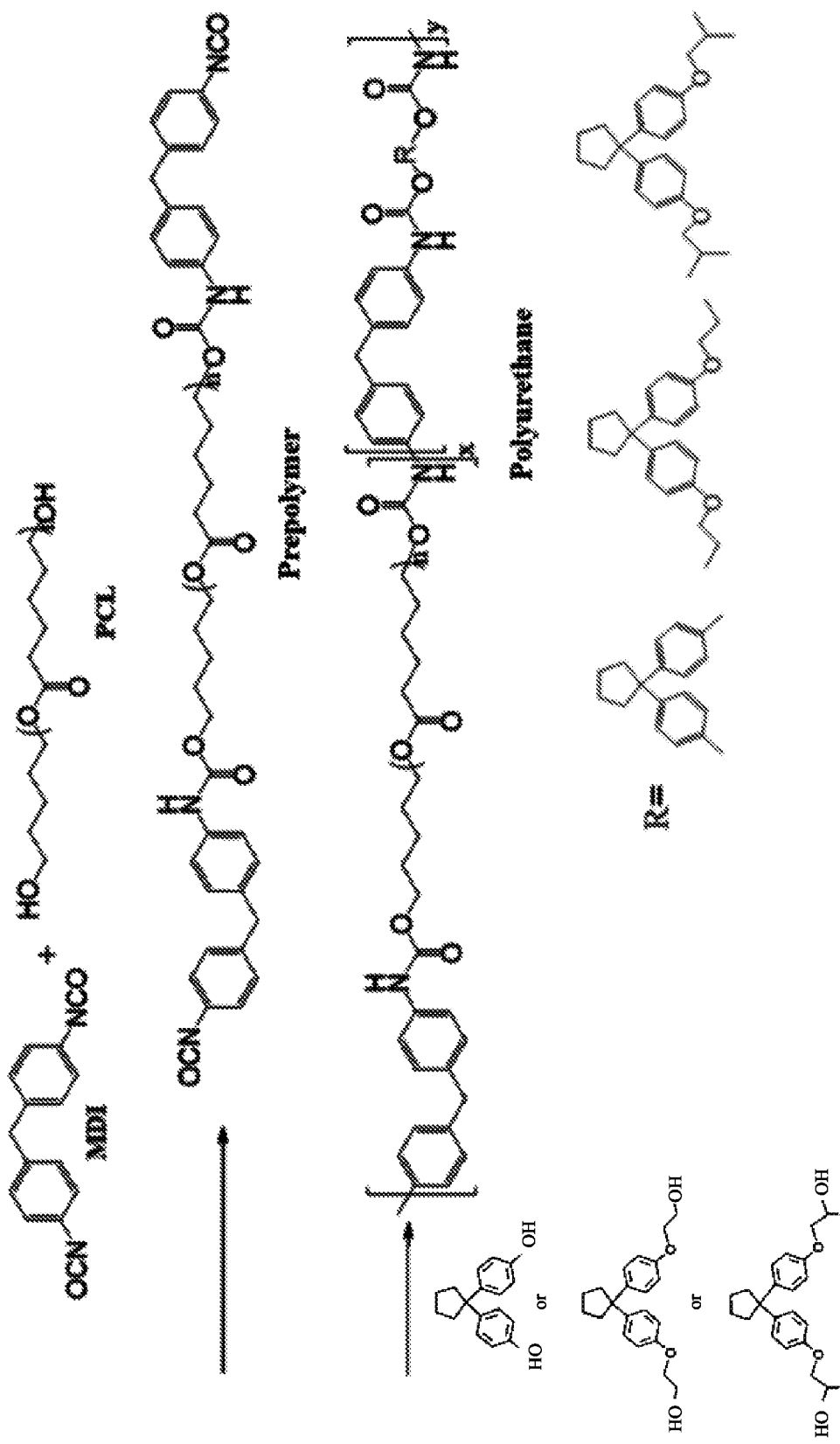
FIG. 6 is a schematic view of the process flow of a method of producing five-carbon ring derivative-containing polyurethane according to an embodiment of the present invention.

Embodiment 4, Embodiment 5, Embodiment 6: Referring to FIG. 6, there is shown a schematic view of the process flow of a method of producing five-carbon ring derivative-containing polyurethane according to an embodiment of the present invention. As shown in the diagram, allow methylene di-p-phenyl diisocyanate (MDI) and polycaprolactone (PCL), with a molecular weight of 3000, to undergo prepolymerization in a solvent, i.e., tetrahydrofuran (THF), at 50° C. for 1.5 hours to obtain prepolymers with a terminal group of isocyanate. Afterward, with reference to the ingredients shown in Table 1, 5-carbon cyclic derivative of embodiment 1, embodiment 2 or embodiment 3 are added to MDI and PCL prepolymers to function as a chain extender for use in polymerization which occurs at 60° C. for 3 hours to form polyurethane. Upon completion of the polymerization, the resultant solution is placed in a teflon baking tray and then baked in an oven at 50° C. to remove the solvent, so as to obtain polyurethane film of embodiment 4, embodiment 5 and embodiment 6. Hard segment content (wt %) shown in Table 1 below is calculated by the expression (MDI weight+ chain extender weight)÷(MDI weight+chain extender weight+PCL weight)×100%.

Comparison 1: comparison 1 is the same as embodiment 4, embodiment 5, and embodiment 6 except for the following: in comparison 1, the chain extender is bisphenol A (BPA), which is polyurethane without any 5-carbon cyclic derivative structure. Comparison 1, embodiment 4, embodiment 5, and embodiment 6 are compared and contrasted in Table 1 below.

TABLE 1

| sample | chain extender | | | | PCL (mole) | MDI (mole) | hard segment content wt % |
| --- | --- | --- | --- | --- | --- | --- | --- |
| | BPA | embodiment 1 | embodiment 2 | embodiment 3 | | | |
| comparison 1 | 1 | 0 | 0 | 0 | 0.17 | 1.17 | 50 |
| embodiment 4 | 0 | 1 | 0 | 0 | 0.18 | 1.18 | 50 |
| embodiment 5 | 0 | 0 | 1 | 0 | 0.23 | 1.23 | 50 |
| embodiment 6 | 0 | 0 | 0 | 1 | 0.22 | 1.22 | 50 |

The dried polyurethane films of embodiment 4, embodiment 5 and embodiment 6 are dissolved in N-methyl-2-pyrrolidone (NMP) to measure and analyze their weight-average molecular weight (Mw), number-average molecular weight (Mn), and molecular weight polydispersity index. The findings are shown in Table 2 below.

TABLE 2

| sample | Mw | Mn | PDI |
| --- | --- | --- | --- |
| comparison 1 | 25946 | 6699 | 3.873 |
| embodiment 4 | 161761 | 64114 | 2.523 |
| embodiment 5 | 164100 | 70824 | 2.317 |
| embodiment 6 | 162539 | 52129 | 3.118 |

Figure 7:
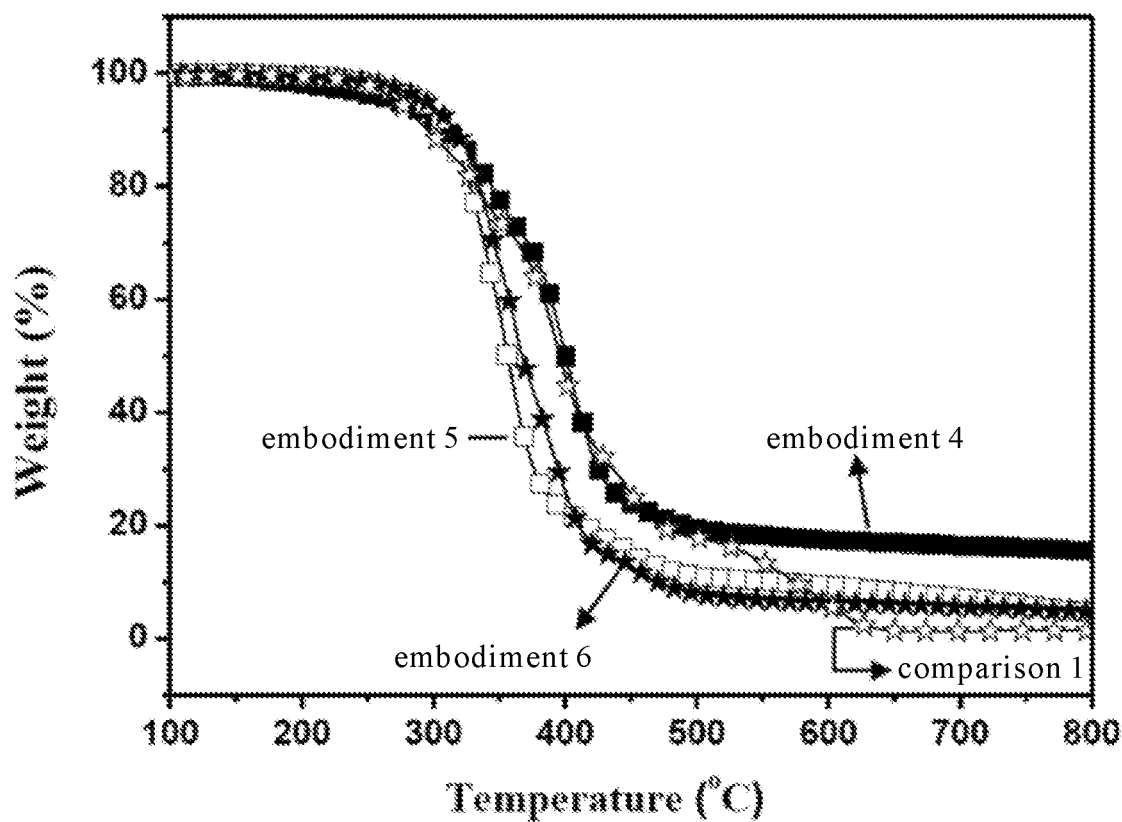
FIG. 7 shows the findings in TGA analysis of five-carbon ring derivative-containing polyurethane according to an embodiment of the present invention.
Figure 8:
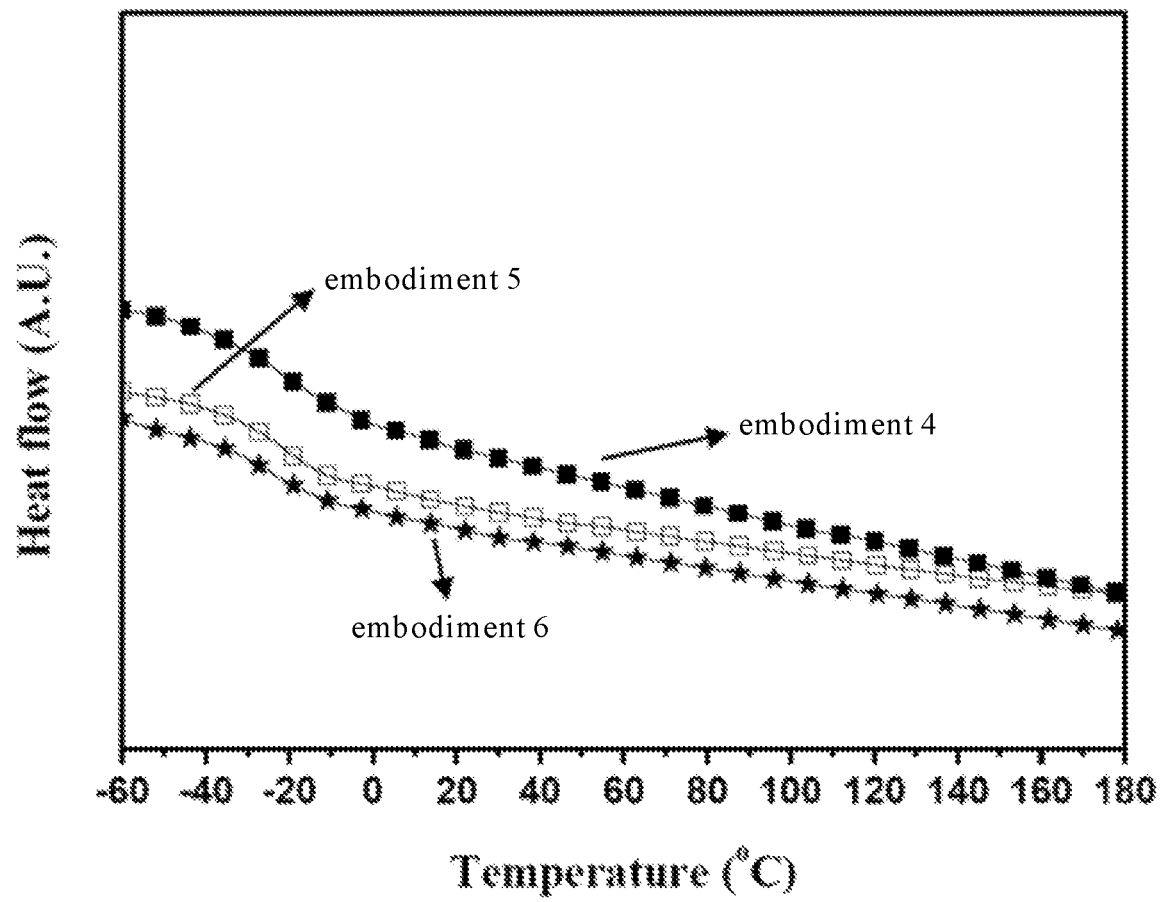
FIG. 8 shows the findings in DSC analysis of five-carbon ring derivative-containing polyurethane according to an embodiment of the present invention.

Referring to FIG. 7 and FIG. 8, there are shown the findings in TGA analysis and DSC analysis of five-carbon ring derivative-containing polyurethane according to an embodiment of the present invention, respectively. As shown in the diagrams, introduction of 5-carbon cyclic derivative long carbon chains is accompanied by a reduction in the thermal degradation temperature.

Figure 9:
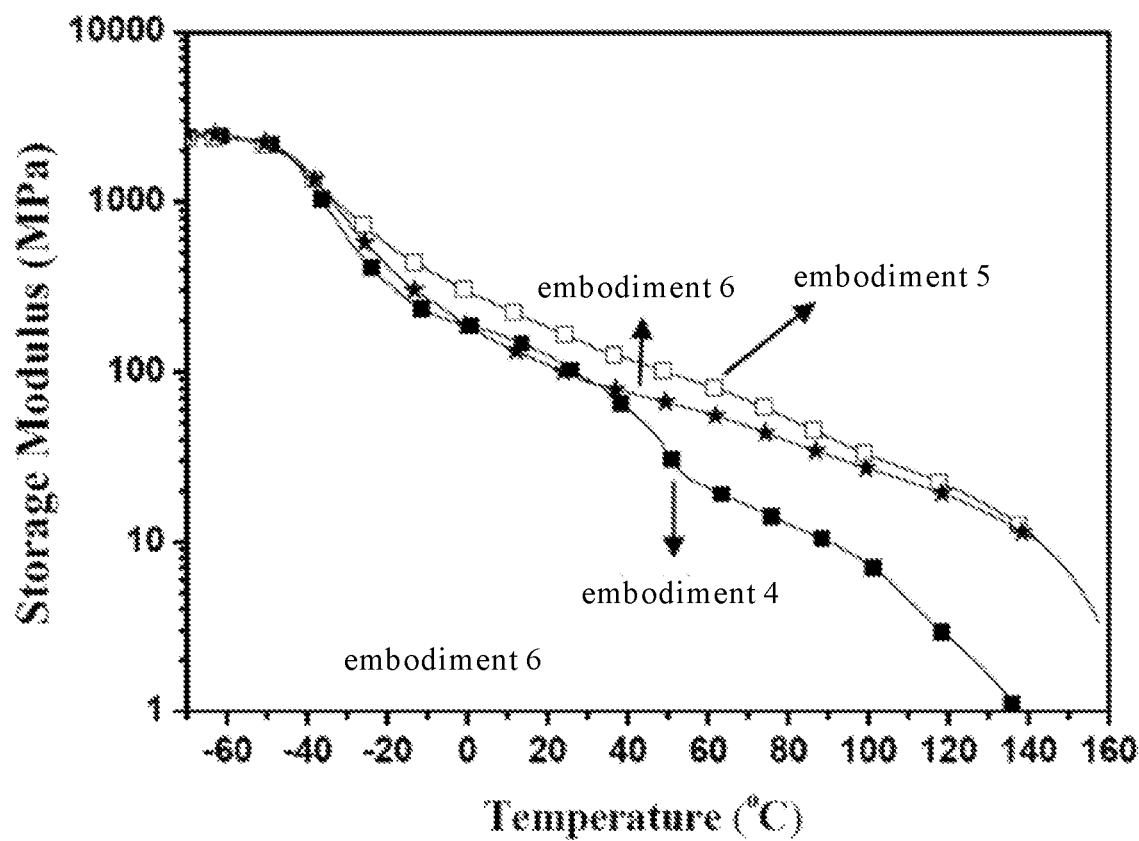
FIG. 9 shows the findings in DMA analysis of five-carbon ring derivative-containing polyurethane according to an embodiment of the present invention.

Referring to FIG. 9, there is shown the findings in DMA analysis of five-carbon ring derivative-containing polyurethane according to an embodiment of the present invention. The storage modulus E' of samples each 20 mm long, 10 mm wide, and 2 mm thick and made of a cured product is assayed with a dynamic mechanical analyzer (DMA) at a temperature rising rate of 5° C./min and frequency of 1 Hz. As shown in FIG. 9, curves of the storage modulus E' indicate that both embodiment 5 and embodiment 6 have higher storage modulus E' of polyurethane film than embodiment 4.

A method of producing a five-carbon ring derivative-containing polyurethane according to the present invention not only uses a green, environment-friendly material (dicyclopentadiene, DCPD) to produce glycol monomers of a five-carbon ring-containing compound, but also uses the monomers as a chain extender for use in polymerization to form polyurethane and thereby produce a five-carbon ring derivative-containing polyurethane material. Unlike the prior art which uses high-polarity, high-boiling-point dimethylformamide (DMF) or dimethylacetamide (DMAc) as a synthetic solvent for use in polymerization to form polyurethane, the present invention provides a production method which involves carrying out polymerization in a solvent (such as tetrahydrofuran or acetone) with a low boiling point and low toxicity to form polyurethane which has a high molecular weight, thereby widening the application of the production method of the present invention.

The above embodiments are illustrative of the features and effects of the present invention rather than restrictive of the scope of the substantial technical disclosure of the present invention. Persons skilled in the art may modify and alter the above embodiments without departing from the spirit and scope of the present invention. Therefore, the scope of the protection of rights of the present invention should be defined by the appended claims.

What is claimed is:

1. A method of producing a five-carbon ring derivative-containing polyurethane, the method comprising the steps of:
   (a) allowing a diisocyanate compound to react with a polyethylene glycol compound and thus produce a prepolymer; and
   (b) allowing the prepolymer to react continuously with a 5-carbon cyclic compound expressed by formula (I) or formula (II) below,

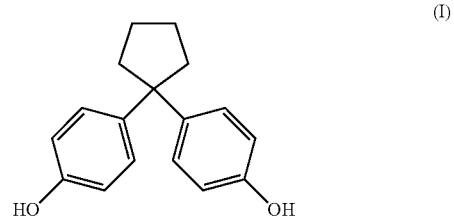 [SMILES: Oc1ccc(C2(c3ccc(O)cc3)CCCC2)cc1]

(I)

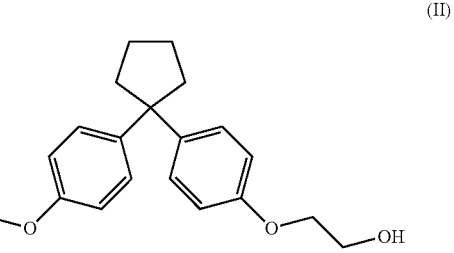

(II)

and thus produce a five-carbon ring derivative-containing polyurethane.

2. The method of claim 1, wherein, the diisocyanate compound of step (a) is one selected from the group consisting of methylene di-p-phenyl diisocyanate, hexamethylene diisocyanate, isophorone diisocyanate, and dicyclohexylmethane-4-4'-diisocyanate.

3. The method of claim 1, wherein the five-carbon ring derivative-containing polyurethane has a molecular weight of 55,000~200,000.

4. The method of claim 1, wherein the diisocyanate compound is methylene di-p-phenyl diisocyanate, the polyethylene glycol compound is polycaprolactone, and the five-carbon ring derivative-containing polyurethane is a polymer expressed by formula (IV) below,

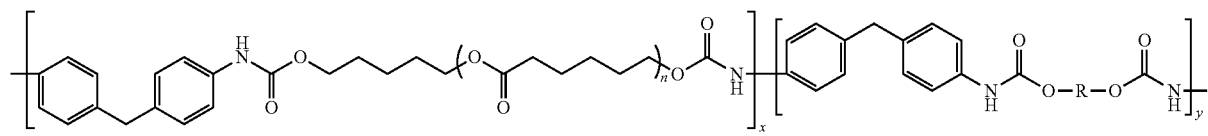
where R is one of groups expressed by formulas below,
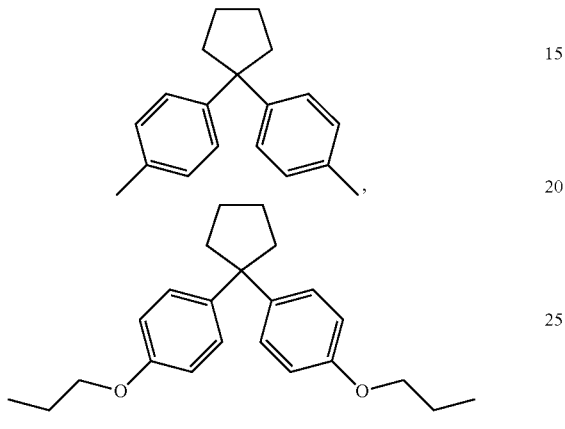
wherein y>0.
5. The method of claim 4, wherein n segment has a molecular weight of 1,000~4,000.
6. The method of claim 4, wherein x segment to y segment weight ratio is expressed by y/(x+y)=0.4~0.6.
7. A five-carbon ring derivative-containing polyurethane, produced by the method of claim 1.
* * * * *